(12) United States Patent
Leu et al.

(10) Patent No.: US 6,270,499 B1
(45) Date of Patent: Aug. 7, 2001

(54) BONE FIXATION DEVICE

(75) Inventors: Dieter Leu, Rickenbach; Peter Däscher, Davos Platz, both of (CH)

(73) Assignee: Synthes (U.S.A.), Paoli, PA (US)

( * ) Notice: Subject to any disclaimer, the term of this patent is extended or adjusted under 35 U.S.C. 154(b) by 0 days.

(21) Appl. No.: 09/529,718

(22) PCT Filed: Oct. 20, 1997

(86) PCT No.: PCT/CH97/00392

§ 371 Date: Apr. 19, 2000

§ 102(e) Date: Apr. 19, 2000

(87) PCT Pub. No.: WO99/20195

PCT Pub. Date: Apr. 29, 1999

(51) Int. Cl.⁷ .................................................. A61B 17/72
(52) U.S. Cl. .................. 606/64; 606/62; 606/67
(58) Field of Search ................. 606/60, 62, 63, 606/64, 65, 67, 68, 72, 73

(56) References Cited

U.S. PATENT DOCUMENTS

| 5,035,697 | 7/1991 | Frigg | 606/67 |
| 5,122,141 | 6/1992 | Simpson et al. | 606/62 |
| 5,531,748 | 7/1996 | de la Caffiniere | 606/62 |
| 5,653,709 | 8/1997 | Frigg | 606/64 |

FOREIGN PATENT DOCUMENTS

| 43 41 677 C1 | 7/1995 | (DE) . |
| 0 447 824 A1 | 9/1991 | (EP) . |
| WO 94/13219 | 6/1994 | (WO) . |
| WO 95/26688 | 10/1995 | (WO) . |

*Primary Examiner*—David O. Reip
(74) *Attorney, Agent, or Firm*—Pennie & Edmonds LLP

(57) ABSTRACT

A bone fracture fixation device according to the present invention includes an intramedullary nail and an intramedullary nail head. The intramedullary nail head can be set and fixed on the proximal end of the intramedullary nail and has at least one bore which extends transversely to the central axis of the intramedullary nail for form-fittingly receiving at a stable angle a bone fastener. At least one threaded bore is provided between the distal end and the proximal end of the intramedullary nail.

20 Claims, 7 Drawing Sheets

BONE FIXATION DEVICE

FIELD OF THE INVENTION

This invention concerns a device for fixation of bone fractures.

BACKGROUND OF THE INVENTION

When the head of the tibia is fractured, a load-bearing fracture surface must be reconstructed. The tibia is the only bone in the body where there is a continuous transition from a cubic bone with a load-bearing articular face into a tubular bone. In the area of the head of the tibia, load forces acting axially on the proximal articular tibia surfaces are converted continuously into a load on the tubular bone. No specific implants for these conditions have been available so far. An ideal load-bearing device for the head of the tibia must take these specific conditions into account.

In the related art various straight plates and angle plates as well as intramedullary nails are available for treating fractures of the head of the tibia. However, all these implants are designed for strong young bones and so far have been used mainly to treat accident-related fractures (sports and athletic accidents, labor accidents and traffic accidents).

However, due to aging of the general population and also the level of activity being pursued by the elderly population, the medical profession is increasingly confronted with the need for treating fractures in osteoporotic bones.

Osteoporosis is a growing problem in health care. The percentage of patients over 80 years of age has increased drastically, so there has also been a definite increase in fractures in patients with osteoporosis. Fractures of the proximal and distal tibia, the proximal and distal femur as well as the proximal humerus and the distal ulna and radius are of primary concern.

Previous osteosynthetic implants according to the related art are not very suitable for use with osteoporotic bones where the cortex is thin and spongy tissue is of an inferior quality. It is often difficult to correctly reposition fragments when the cortex is thin. Fixation and/or immobilization of a repositioned fracture is often extremely problematical in osteoporotic bones because osseous anchoring of the implants is difficult.

Regardless of bone quality, implants that are truly optimized for treatment of proximal tibia fractures and in particular fractures of the head of the tibia have not been available. Only a few slightly modified plates and intramedullary nails are available.

European Patent No. 118,778 describes a locking nail with an elongated hollow body which is rounded at the proximal end and has an end with a widened head. In addition, at least two cross bores are provided in the body to accommodate one bone screw in each. The cross-sectional profile of the body forms a closed ring over its circumference.

Another locking nail made of solid material is disclosed in European Patent No. 447,824 FRIGG, where the proximal end part has a cross-sectional area with a trigonal shape in both the anterior and the posterior halves while being approximately quadratic as a whole. The distal end part has a cross-sectional area which is approximately trigonal in the anterior half and is approximately hemispherical in the posterior half. This specific design of the intramedullary nail according to this invention causes a high rotational stability in the proximal spongy part of the tibia while on the other hand permitting the most optimal possible adaptation to the geometry of the medullary space in the distal confocal part of the tibia.

Another locking nail is known from German Patent No. 43 41 677 SCHROEDER The nail body is rounded at the distal end and has a proximal concave end. Cross bores to accommodate one bone screw each are arranged in the nail body. In addition, the nail body is made of a solid material and has a funnel-shaped opening at least on one side of each cross bore.

SUMMARY OF THE INVENTION

The object of this invention is to create a device for fixation of bone fractures that can be used for optimal treatment of the following fractures even in patients with osteoporosis:

1. Fractures of the tibia shaft:
   fractures of the proximal tibia shaft
   ipsilateral fractures of the head of the tibia
2. Fractures of the head of the tibia:
   fractures of the medial and lateral tibia plateau
   fractures of the dorsal articular portions of the proximal tibia
   ipsilateral tibia shaft fractures
3. Similar fractures of the distal or proximal femur (which meet the following conditions):
   offering stable fixation even in osteoporosis patients due to optimal (axial) biomechanical positioning and fixation at a stable angle with a large contact area between bone and implant
   easy and simple to handle (e.g., by avoiding posterior access in dorsoproximal fractures of the tibia head);
   suitable for both right and left tibia and medial and lateral tibia plateau.

Another object of this invention is to be able to secure a bone fragment by means of a bone screw running across the axis of the intramedullary nail and tighten it against the intramedullary nail, so an intrafragment pressure can be produced.

This invention achieves in general the object formulated here with a device having the features of claim 1.

An intramedullary nail in the head of the tibia is in the optimal position biomechianically as an axial implant. The intramedullary nail is secured in the medullary space of the tibia by means of pins. If the intramedullary nail is also tightened to the ventral cortex, the contact area between osteoporotic bone and implant is increased, and therefore the contact forces are reduced. The head of the tibia can be reconstructed using screws which are screwed into the intramedullary nail at a stable angle. Biomechanically, the intramedullary nail with the tibia head screws which are screwed into it at a stable angle thus assumes the function of an intramedullary angle plate. This combines the advantages of an axial implant (intramedullary nail) with the advantages of an implant at a stable angle (angle plate).

With the implant according to this invention in contrast with known osteosynthesis systems, the load-bearing element is first positioned in the biomechanical position and then is anchored in intact bone. The fracture is then repositioned on this fixedly anchored load-bearing element and secured in a position at a stable angle. Since the fracture is secured in a fixedly anchored load-bearing element in a position at a stable angle, the quality of the bone (porosity) is of secondary importance.

A preferred refinement of this invention consists of the fact that the intramedullary nail has a bore running across the central axis in the area of the distal end as well as in the area of the proximal end in order to be able to lock the intramedullary nail in position.

The head of the intramedullary nail has one or preferably at least two or more bores whose axes may be parallel or divergent and which may have a thread.

The bone fixation means to be inserted in the intramedullary nail head is preferably a bone screw with a screw head and a screw shaft thread, said bone screw preferably having a continuous central channel. The thread near the screw head preferably has a smaller pitch than the thread of the screw shaft. An unthreaded section of shaft is preferably provided between the two different threads. It is thus possible to tighten a bone fragment secured with this bone screw to produce an intrafragment pressure.

The tip of this bone screw is preferably designed to be self-tapping and self-cutting. This simplifies the procedure.

Instead of bone screws, a blade or a plate may also be used as bone fixation means. The blade or the plate is preferably slotted or has a threaded bore to accommodate pins or screws.

This makes it possible to achieve an intramedullary screw connection at a stable angle.

BRIEF DESCRIPTION OF THE DRAWINGS

This invention and refinements of this invention are explained in greater detail below on the basis of the partially schematic diagrams of several embodiments, which show.

DETAILED DESCRIPTION OF THE PREFERRED EMBODIMENTS

Figure 1:
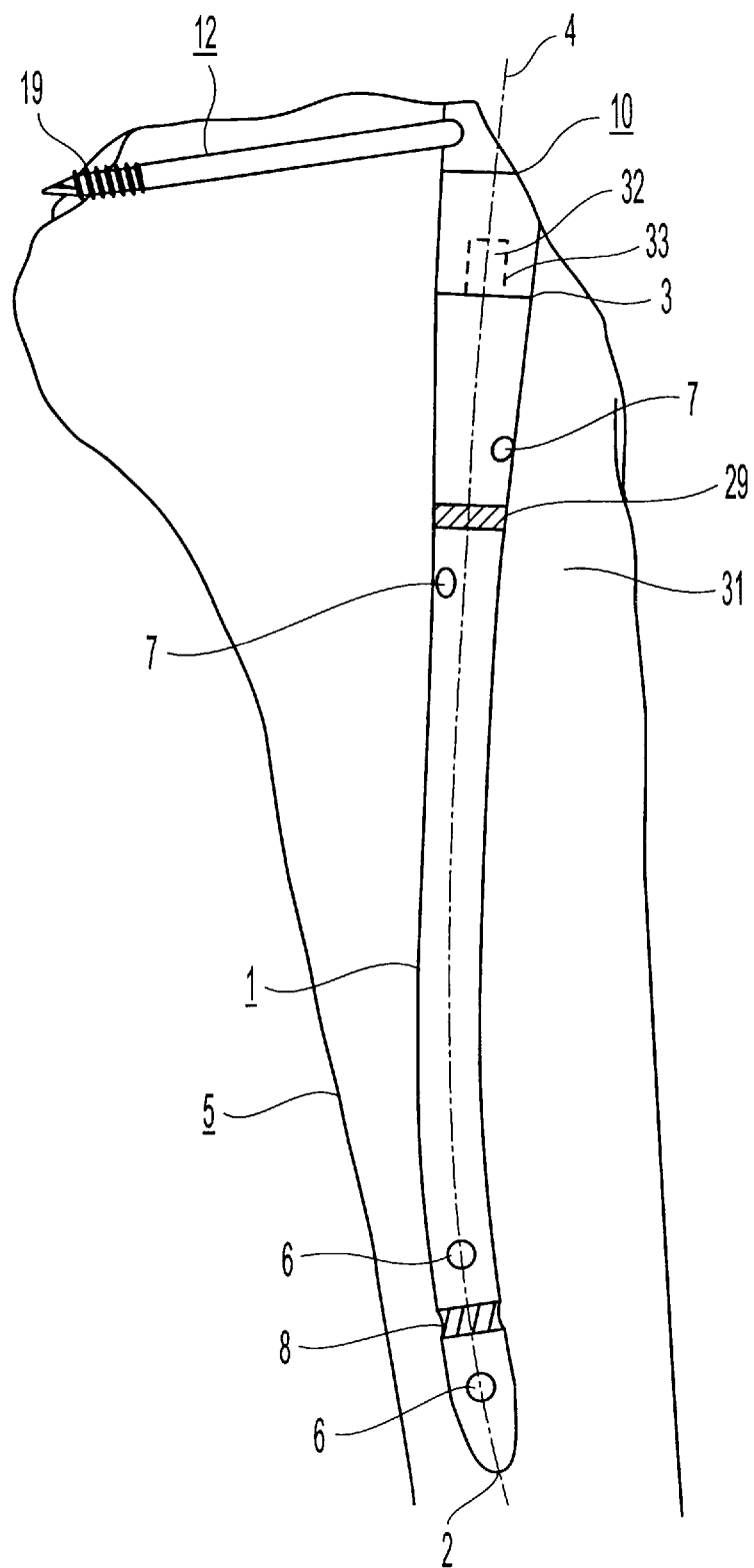
FIG. 1 is a longitudinal section through the device according to this invention implanted in bone with an intramedullary nail head for tibia head screws.

The device according to this invention as illustrated in FIG. 1 comprises an intramedullary nail 1 with a distal end 2, a proximal end 3 and a central axis 4. Intramedullary nail 1 has a slight curvature, distal end 2 being blunt. In the area of distal end 2, there are two bores 6 running across the central axis 4 into which locking pins can be inserted. Between the two bores 6 there is a threaded bore 8 running anteroposteriorly (approximately corresponding to the plane of the drawing) which serves to accurately position the intramedullary nail 1 in the intramedullary space of bone 5.

In the area of proximal end 3 there are two bores 7 running across the central axis 4 into which additional locking pins can be inserted. With a third threaded anteroposterior bore 29, the intramedullary nail can be tightened to the ventral cortex 31. This allows accurate positioning of intramedullary nail 1 in the intramedullary space.

Figure 2:
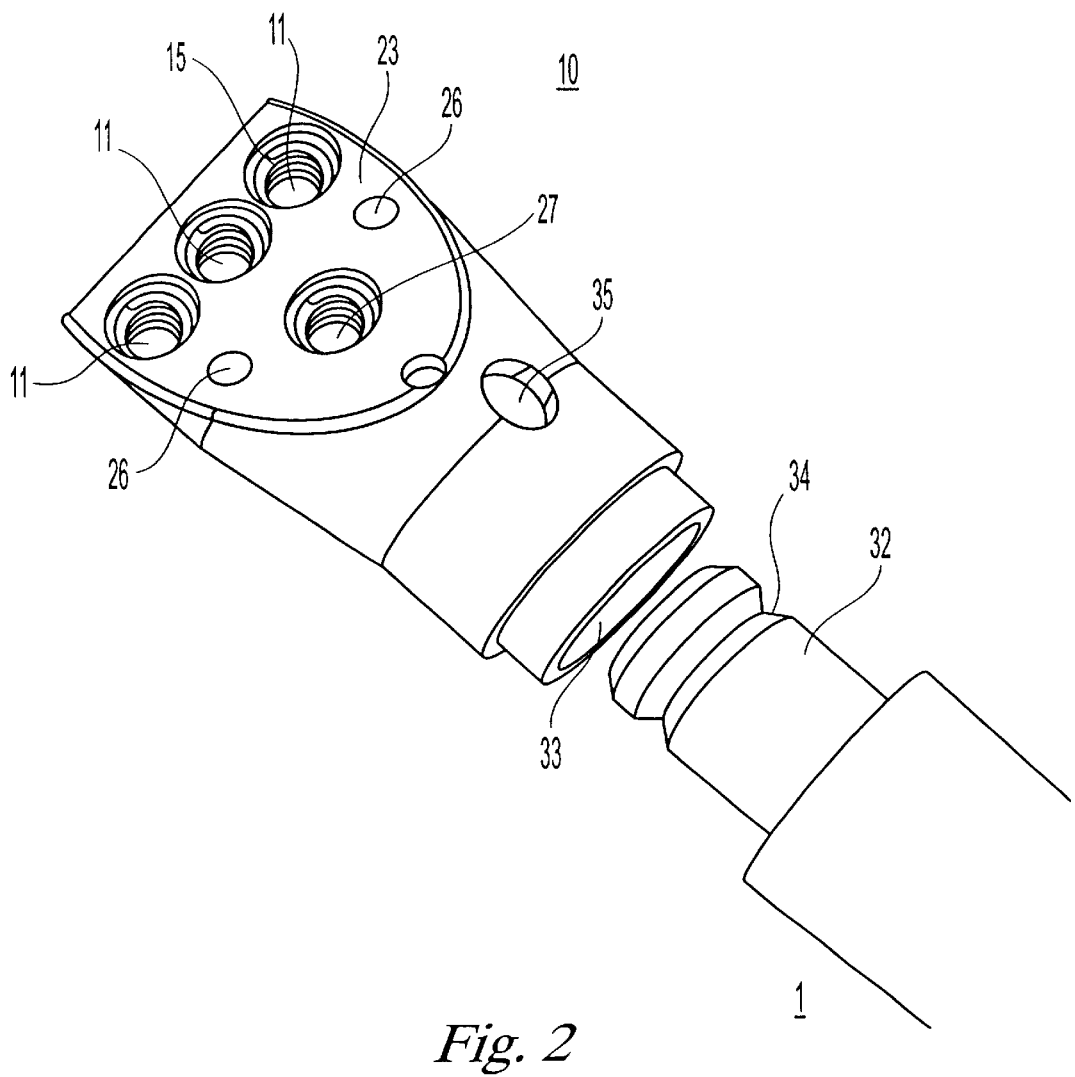
FIG. 2 is an enlarged perspective diagram of the intramedullary nail head of FIG. 1 with the head rotated 90°.
Figure 3:
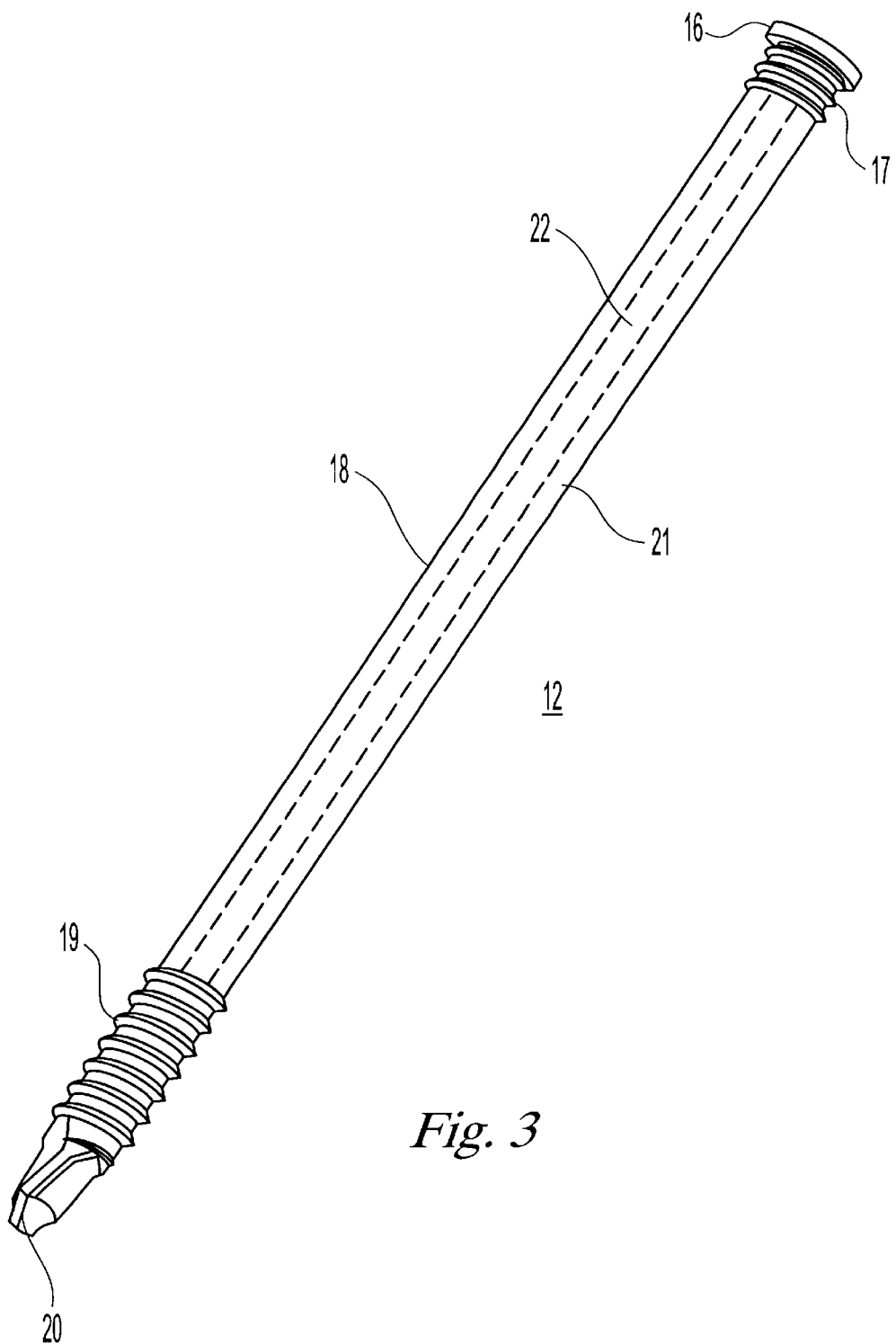
FIG. 3 is an enlarged perspective diagram of the tibia head screw from FIG. 1.

As shown in detail in FIG. 2, the intramedullary nail head 10 is in the shape of a cylinder cut on the diagonal, where the diagonal face 23 has three bores 11 side by side passing through it with parallel or divergent axes. Bores 11 of intramedullary nail head 10 all have a thread 15 to allow them to accommodate bone screws 12 (FIG. 3) having a screw head 16 with a matching thread 17. Bone screws 12 have a screw shaft 18 with two threaded sections 19 and 17. The pitch of thread 19 at the tip 20 of the screw is larger than the thread 17 near the screw head. Bone screws 12 also have a continuous central channel 22 through which guide wires can be passed. Between the two threads 17, 19 there is an unthreaded section 21 of shaft. Tip 20 of the screw is designed to be self-taping and self-cutting.

Additional bores 26, 27 are provided on the diagonal face 23 to permit attachment of the usual intramedullary nail driving devices to it in a detachable manner.

The intramedullary nail head 10 may be attached to a corresponding cylindrical stud 32 on the proximal end 3 of the intramedullary nail 1 as shown in FIGS. 1 and 2 with a cylindrical bore 33. Stud 32 may have longitudinal grooves or channels 34 which engage in corresponding elements (grooves or channels) in the interior of bore 33 to secure the two parts 1, 10 to prevent twisting, and the definitive axial fixation of the two parts 1, 10 can be accomplished by inserting a fixation screw into the transverse bore 35 of intramedullary nail head 10.

Figure 4:
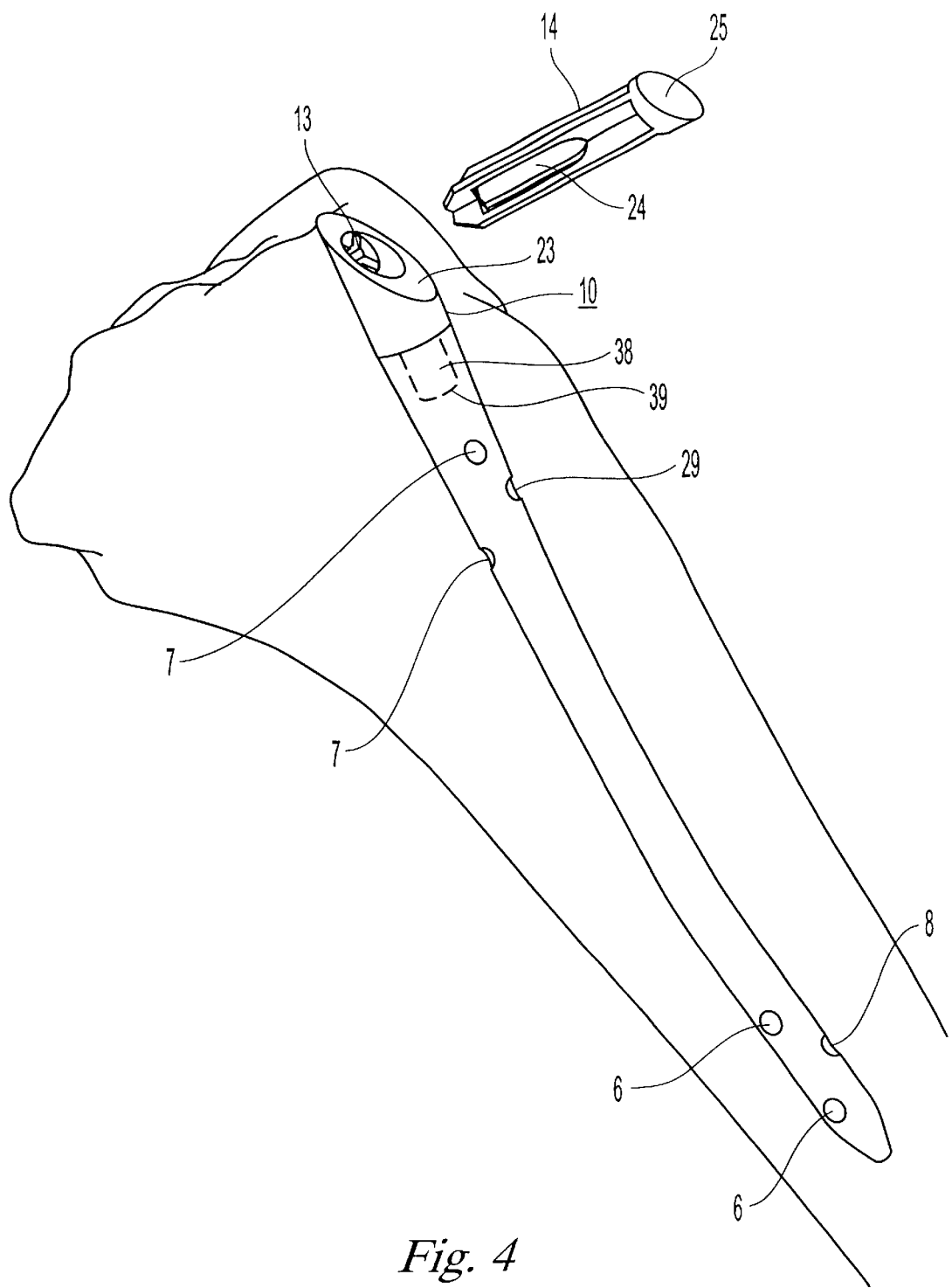
FIG. 4 is a perspective diagram of a device according to this invention implanted in bone with an intramedullary nail head for an intramedullary tibia head cross plate.
Figure 5:
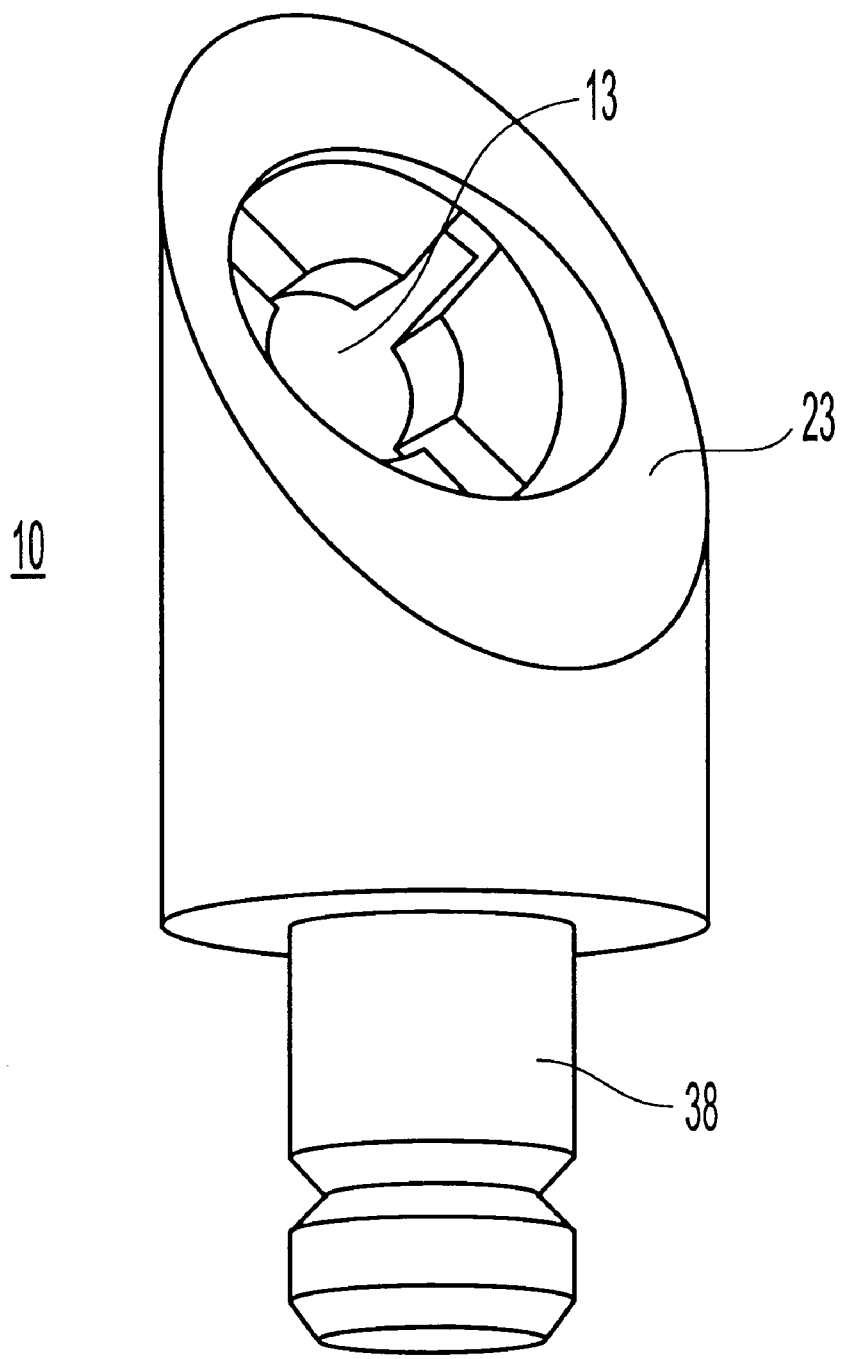
FIG. 5 is a perspective diagram of an intramedullary nail head having a cross recess.

With another embodiment of this invention illustrated in FIG. 4, instead of the bone screw 12, a crossed blade 14 is provided as the bone fixation means which has a recess 24 to accommodate pins or screws. To accommodate this blade 14, intramedullary nail head 10 is also modified in comparison with the embodiment according to FIGS. 1 and 2. As illustrated in FIG. 5, the intramedullary nail head 10 in this variant has a single cross recess 13 which is slightly recessed in diagonal face 23 instead of having three bores 11. Another modification in this embodiment of intramedullary nail head 10 consists of the fact that a stud 38 is provided instead of a cylindrical bore 33 (FIG. 2). Accordingly, the respective intramedullary nail 1 has a bore 39 instead of a stud.

Figure 6:
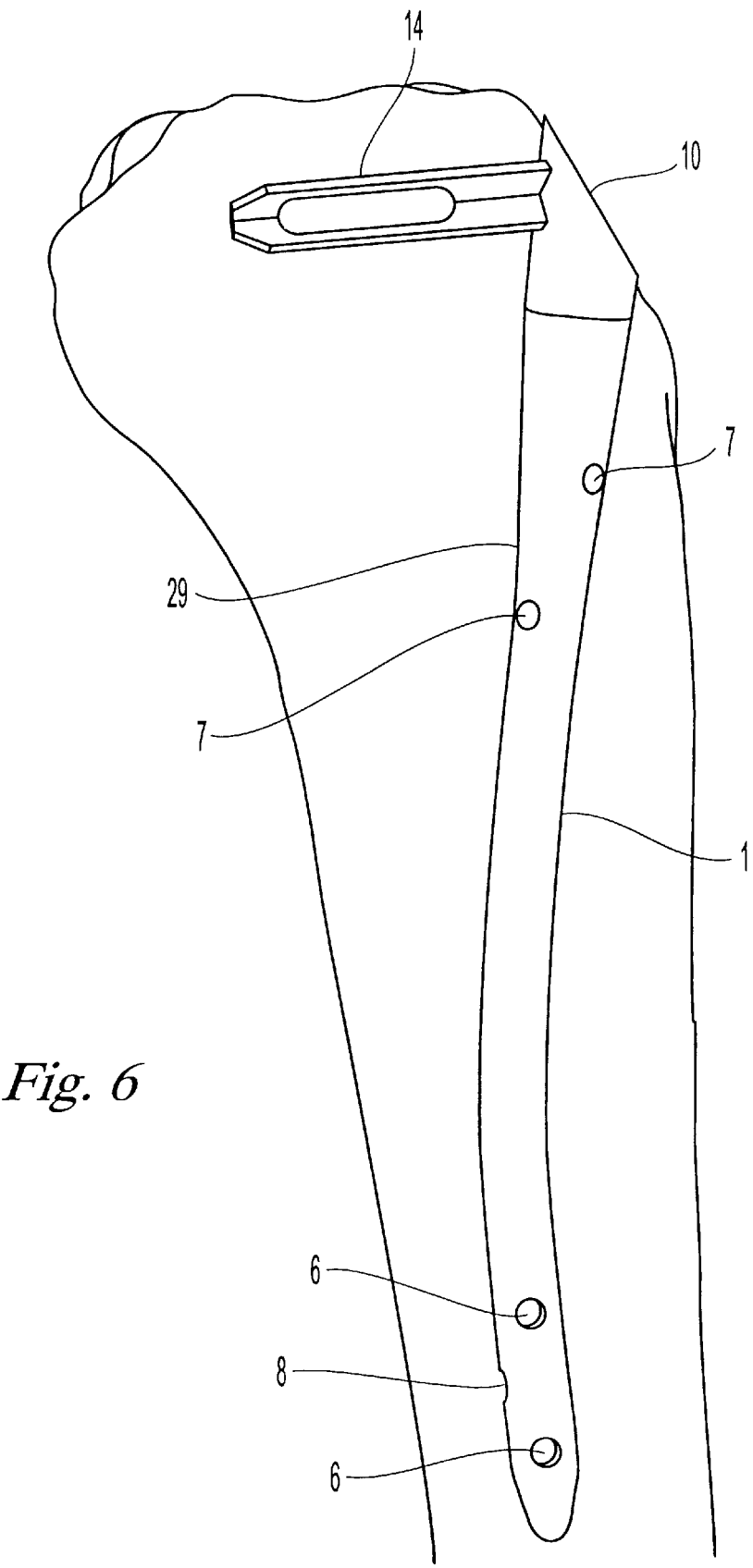
FIG. 6 is a perspective diagram of a device of FIG. 4 fully implanted.

Crossed blade 14 can be inserted into cross recess 13 until its head 25 is flush with diagonal face 23, thus reaching the position illustrated in FIG. 6.

Figure 7:
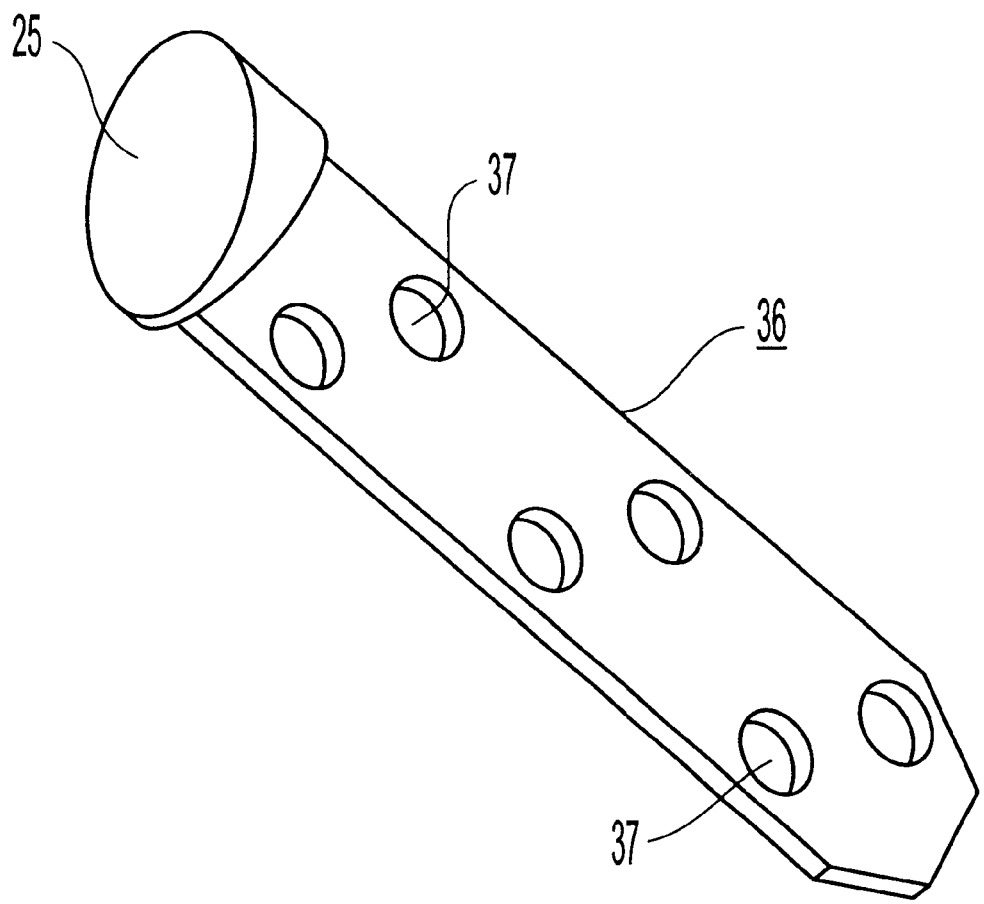
FIG. 7 is a perspective diagram of another embodiment of a tibia head bone plate.

Instead of blade 14, a bone plate 36 may also be used, as illustrated in FIG. 7, having threaded bores 37 which may be arranged in various ways in plate 36.

Head 25 is designed in the same way as in the case of blade 14 so that a form-fitting insertion of bone plate 36 into cross slit 13 at a stable angle is guaranteed (FIG. 4).

What is claimed is:

1. A fracture fixation device for fixation of bone fractures comprising:

an intramedullary nail with a distal end, a proximal end, and a central axis and having a threaded bore near the distal end for positioning the intramedullary nail in a medullary canal of bone;

an intramedullary nail head operatively associated with the intramedullary nail and having at least one through hole transverse to the central axis of the intramedullary nail; and a screw configured and dimensioned for insertion in the at least one through hole of the intramedullary nail head and having a threaded head portion and a threaded shaft portion, the screw head threaded portion having a pitch smaller than that of the threaded shaft portion for bone fragment compression, wherein the at least one through hole accommodates the screw at a fixed angle.

2. The fracture fixation device of claim 1 wherein the intramedullary nail head is detachable from the intramedullary nail.

3. The fracture fixation device of claim 2 wherein the intramedullary nail head has a body and a stem configured and dimensioned for coupling with the proximal end of the intramedullary nail.

4. The fracture fixation device of claim 3 wherein the proximal end of the intramedullary nail includes a cylindrical extension configured and dimensioned for insertion in the stem of the intramedullary nail head.

5. The fracture fixation device of claim 4 wherein the cylindrical extension has a groove and the stem has a fastener hole for receiving a fastener, the fastener cooperating with the groove to secure the intramedullary nail head to the intramedullary nail.

6. The fracture fixation device of claim 1 wherein the intramedullary nail head has the shape of a cylinder with one end cut at an angle of about 45°.

7. The fracture fixation device of claim 1 wherein the intramedullary nail head is integral with the intramedullary nail.

8. The fracture fixation device of claim 1 wherein the intramedullary nail has at least one aperture near the distal end for receiving a locking pin.

9. The fracture fixation device of claim 1 wherein the intramedullary nail has at least one aperture near the proximal end for receiving a locking pin.

10. The fracture fixation device of claim 1 wherein the at least one through hole comprises three through holes.

11. The fracture fixation device of claim 10 wherein the three through holes have divergent axes.

12. The fracture fixation device of claim 10 wherein the three through holes have parallel axes.

13. The fracture fixation device of claim 1 wherein the at least one through hole is at least partially threaded.

14. The fracture fixation device of claim 1 wherein the bone screw has a continuous central channel.

15. The fracture fixation device of claim 1 wherein at least a portion of the screw is unthreaded.

16. The fracture fixation device of claim 1 wherein the screw is a self-tapping and self-cutting screw.

17. The fracture fixation device of claim 1 wherein the intramedullary nail includes a recess for receiving a blade having a body with a cutout for receiving fasteners to secure the blade to bone.

18. The fracture fixation device of claim 17 wherein the recess is slotted for receiving the body of the blade.

19. The fracture fixation device of claim 1 wherein the intramedullary nail includes a recess for receiving a plate having a plurality of plate holes for receiving fasteners to secure the plate to bone.

20. The fracture fixation device of claim 1 wherein the intramedullary nail has a threaded bore near the proximal end.

* * * * *